United States Patent
Wang et al.

(10) Patent No.: US 11,517,702 B1
(45) Date of Patent: Dec. 6, 2022

(54) INTEGRATED OXYGEN SUPPLY DEVICE

(71) Applicant: Telesair, Inc., Irvine, CA (US)

(72) Inventors: Qing Wang, Irvine, CA (US); Yong Liu, Irvine, CA (US)

(73) Assignee: TELESAIR, INC., Irvine, CA (US)

( * ) Notice: Subject to any disclaimer, the term of this patent is extended or adjusted under 35 U.S.C. 154(b) by 0 days.

(21) Appl. No.: 17/569,461

(22) Filed: Jan. 5, 2022

(51) Int. Cl.
*A61M 16/10* (2006.01)
*A61M 16/00* (2006.01)
*A61M 16/12* (2006.01)

(52) U.S. Cl.
CPC ...... *A61M 16/101* (2014.02); *A61M 16/0003* (2014.02); *A61M 16/12* (2013.01); *A61M 2202/0208* (2013.01)

(58) Field of Classification Search
CPC .................................................. A61M 16/101
See application file for complete search history.

(56) References Cited

U.S. PATENT DOCUMENTS

| | | |
|---|---|---|
| 11,135,390 B1 | 10/2021 | Wang |
| 2010/0116270 A1 | 5/2010 | Edwards et al. |
| 2011/0247620 A1 * | 10/2011 | Armstrong ............ B01D 53/047 128/207.18 |
| 2012/0006326 A1 | 1/2012 | Ahmad |
| 2017/0056613 A1 * | 3/2017 | Cortez, Jr. ............ A61M 16/16 |
| 2018/0023553 A1 * | 1/2018 | Winter .................... F04B 53/22 417/222.2 |
| 2021/0228832 A1 * | 7/2021 | Parrish ................ A61M 16/049 |

* cited by examiner

*Primary Examiner* — Margaret M Luarca
*Assistant Examiner* — Cana A Gallegos
(74) *Attorney, Agent, or Firm* — Javalon Law, PC

(57) ABSTRACT

An integrated oxygen supply device that is configured to generate oxygen continuously and release the oxygen non-continuously is provided. In some embodiments, the oxygen generated by the integrated oxygen supply device is stored in a porous material with the integrated oxygen supply device. The delivery of the oxygen produced by integrated oxygen supply device to a patient, in those embodiments, is controlled. In some embodiments, the control of the delivering oxygen is according one or more breathing patterns. The breathing pattern(s) may or may not be a current breathing pattern of the patient. For example, in one embodiment, the breathing pattern is a predetermined breathing pattern with a specified inspiration period followed by a specified expiration period.

10 Claims, 11 Drawing Sheets

INTEGRATED OXYGEN SUPPLY DEVICE

FIELD OF THE INVENTION

The present disclosure relates to oxygen supply device designed and configured for non-professional use environments such as at a patient's home.

BACKGROUND OF THE INVENTION

A medical breathing machine is used to help lungs work. Fundamentally, a medical breathing machine helps a patient to get oxygen into the lung, and to remove carbon dioxide from the body. One of the most widely used breathing machine is high flow nasal canula (HFNC). High Flow Nasal Cannula (HFNC) is one kind of oxygen supply device providing oxygen therapy to respiratory function comprised patients and is recommended by the World Health Organization (WHO) and US National Institutes of Health (NIH) as the first device to treat COVID-19 patients. SARS-CoV-2 virus which causes highly contagious COVID-19. Operating HFNC for COVID-19 patients creates enormous risk to health care workers. Over 38,000 healthcare workers were infected by SARA-VoV-2 in Los Angeles hospitals alone.

HFNC machines help patients suffering from limited and impaired breathing capability. Typically, HFNC machines deliver heated and humidified oxygen enriched air flow to patients through a nasal canula. The flow rate of the oxygen air enriched by the HFNC machines is normally higher than the flow rate of normal inspiration air flow rate of a healthy person of the same age group. Clinical results indicate that HFNC is helpful to those patients who suffer from a variety of indications, including hypoxemic respiratory failure due to pneumonia, post-extubation, pre-oxygenation prior to intubation, acute pulmonary edema, etc.

An oxygen supply device is a device that supplies an oxygen-enriched gas flow. An oxygen supply device can be used in health care institutions to supply oxygen to patients for treatment of respiratory disorders such as asthma, pneumonia, respiratory distress syndrome, bronchopulmonary dysplasia, chronic obstructive pulmonary disease.

SUMMARY OF THE INVENTION

For achieving one or more of advantages, in accordance with the present disclosure, an integrated oxygen supply device that is configured to generate oxygen continuously and release the oxygen non-continuously is provided. In some embodiments, the oxygen generated by the integrated oxygen supply device is stored in a porous material with the integrated oxygen supply device. The delivery of the oxygen produced by integrated oxygen supply device to a patient, in those embodiments, is controlled. In some embodiments, the control of the delivering oxygen is according one or more breathing patterns. The breathing pattern(s) may or may not be a current breathing pattern of the patient. For example, in one embodiment, the breathing pattern is a predetermined breathing pattern with a specified inspiration period followed by a specified expiration period.

In some embodiments, the integrated oxygen supply device in accordance with the present disclosure includes a heat exchange mechanism to enable heat exchange between a medium around a compressor unit employed by the integrated oxygen supply device and gas to be delivered to the patient. In some embodiments, the integrated oxygen supply device includes a control mechanism enabling adjustment of a concentration level of oxygen delivered by the integrated oxygen supply device to the patient. The adjustment in those embodiments can cause the integrated oxygen supply device to change one or more operations of how concentrate oxygen is generated and conditioned to be delivered to the patient.

In various embodiments, the integrated oxygen supply device comprises an air separation unit, a gas conditioning unit, a gas delivery unit, and/or any other components. In those embodiments, the air separation unit is configured to produce concentrated oxygen from ambient air. In one embodiment, the air separation unit comprises an oxygen concentration component configured to separate nitrogen from ambient air to obtain concentrated oxygen and stores the concentrated oxygen. In those embodiments, the stored concentrated oxygen is controlled to be released from the air separation unit according to a pulsing pattern.

In various embodiments, the gas conditioning unit of the integrated oxygen supply device comprises a blending subunit, a compression subunit, a heating unit, a humidification unit and/or any other components. In various embodiments, the gas delivery unit is configured to deliver a high flow, high oxygen concentration, heated, humidified gas to treated patients through a nasal canula. In one embodiment, the delivery of the air by the gas delivery unit is controlled according to a breathing pattern.

Other objects and advantages of the invention will be apparent to those skilled in the art based on the following drawings and detailed description.

DETAILED DESCRIPTION

Figure 1:
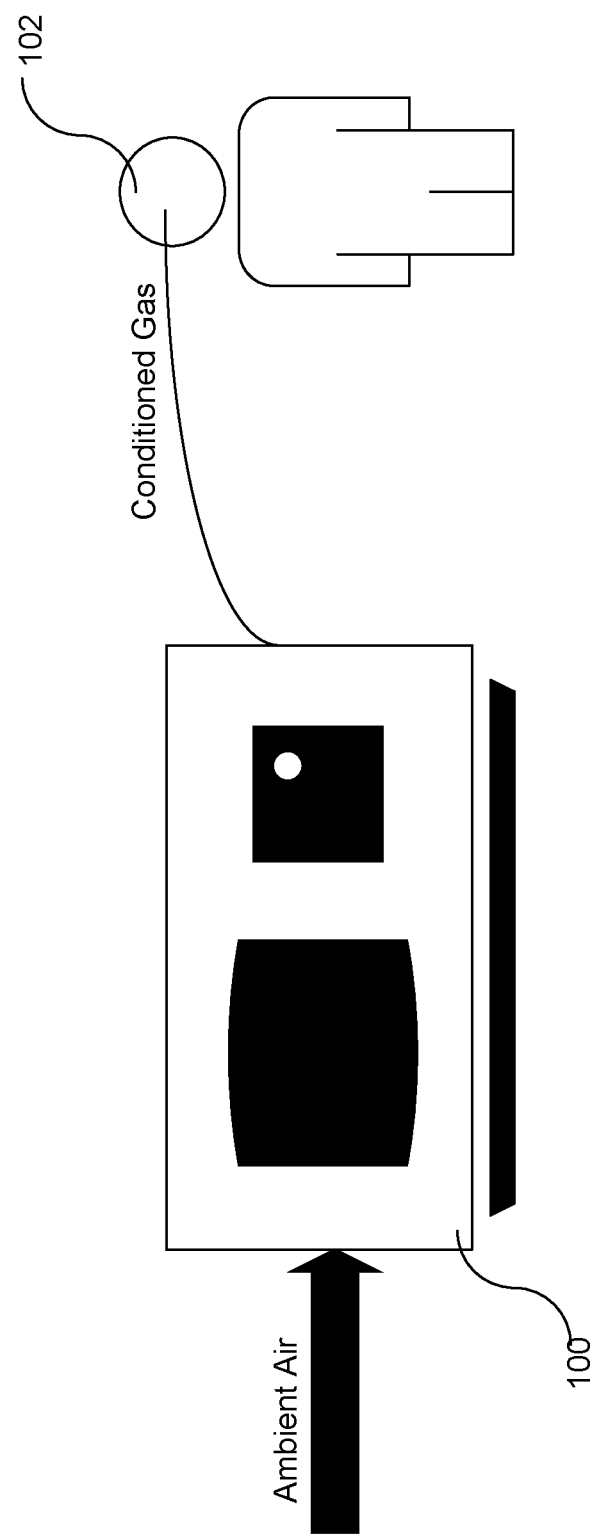
FIG. 1 illustrates generally an integrated oxygen supply device in accordance with the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. For a particular repeated reference numeral, cross-reference may be made for its structure and/or function described and illustrated herein.

Patients with moderate to severe COVID-19 are often present with pneumonia that could lead to hypoxemia. High flow nasal cannula (HFNC) is recommended by the World Health Organization (WHO) and National Institutes of Health (NIH) as a way to provide supplemental oxygen for COVID-19 patients who are hypoxemic. HFNC can provide humidified and body-temperature oxygen from 10-80 L/min to meet patients' demand, and decrease patients' discomfort and work of breathing. It also improves ventilation and oxygenation through the washout of nasopharyngeal dead space. When being compared to conventional oxygen therapy or Noninvasive Positive Pressure Ventilation (NIPPV), HFNC has been demonstrated to decrease 90-day mortality and intubation rate for patients with acute hypoxemic respiratory failure.

As patient's condition changes with time, the settings of HFNC also need to be adjusted accordingly. Due to the nature of high flow, both the WHO and NIH categorized HFNC as an aerosol generating procedure that is defined as a high-risk exposure for HCWs when used on a COVID-19 patient; it becomes a critical battlefront to ensure the safety of HCWs. Studies have shown that frontline HCWs are at least 3 times more likely to be infected. The danger to HCWs is worse when we have limited supplies of PPE. Compared with the HCWs who do not have exposure to patients with COVID-19, HCWs who have inadequate or reused PPE with exposure to patients with COVID-19 have 5-6 times higher infection rate In Los Angeles County, the most populous county in the United states, over 38,000 HCWs and first responders have been confirmed with COVID-19 as of March 2021. COVID-19 pandemic has been a tremendous challenge to our societies as a whole, but hospitals and our frontline HCWs have been under unprecedented stress because of the overwhelming number of COVID-patients and highly contagious nature of COVID-19. During COVID-19 pandemic, different waves of infection in different countries have been happening in different time. Thus, if HFNC treatment can be provided in-home, some or all of above-mentioned risks can be reduced or avoided.

One issue with a current oxygen supply device is that it is not optimal for home use to achieve effective HFNC treatment. A reason that HFNC treatment currently is not assessable to patients at home is a requirement of excessive oxygen supply for effective treating the patients. In some cases, effective HFNC treatment may need flow rate at 40 liter per minute (LPM), and fraction of inspired oxygen (FiO2) at 40%. High pressure oxygen sources such as compressed gas cylinders or fixed medical oxygen plumbing systems (e.g., oxygen tanks) are conventional means for supplying such a level of enriched oxygen to a patient. However, oxygen tanks are expensive, difficult to handle, hard to move and thus are not typically suitable for home use.

As mentioned above, for an effective HFNC treatment, a flow rate of 40 LPM or higher oxygen supply at 40% FIO2 (40/40) or higher is desired. This means an oxygen source of capable of supplying 10 liter per minute pure oxygen is desired to facilitate such a treatment. However, existing oxygen generation devices typically can only generate around 2-5 LPM oxygen from ambient air due to size and/or cost limitations. While some oxygen concentrators are commercially available to generate around 10 LPM oxygen flow, the oxygen is provided by those oxygen concentrators are dry and not palatable to patient. The actual delivered FiO2% is not maintained at the desired value due to the uncertainty in the air entrainment for those oxygen concentrators. A large portion of generated oxygen is wasted when patients is exhaling. Those oxygen concentrators are also typically quite large. Thereby, a challenge for implementing effective HFNC treatment in a non-professional environment such as in a patient's home is how to generate and deliver oxygen, for example, at 40 LPM/40% FIO2 or higher, using an oxygen supply device with a reasonable size and affordable.

One insight provided by the present disclosure is an integrated oxygen supply device comprising an air separation unit, an gas conditioning unit, an gas delivery unit and/or any other components. It should be understood the integrated oxygen supply device in accordance with the present disclosure is a single device having a housing, within which the air separation unit, the gas conditioning unit, and the gas delivery unit are located. Some considerations for the integrated oxygen supply device in accordance with the present disclosure include form factors, costs (affordability), power consumption, efficiency, effectiveness, and/or any other considerations. As mentioned above, for achieving a relatively small form factor of the integrated oxygen supply device in accordance with the present disclosure, a small or reasonably sized oxygen source is desired, such as an air separation unit capable of generating 5 LPM oxygen.

With such an oxygen source in the integrated oxygen supply device, measures or design choices are to be adopted to make up for the above-mentioned LPM gap for achieving an effective treatment. One insight provided by the present disclosure is that flow of an oxygen output from the air separation unit in the integrated oxygen supply device can be controlled. Other considerations are also explored by the inventor(s) to reduce or close this LPM gap. Insights into the other considerations are culminated into other disclosures to enable HFNC treatment at a non-professional environment such as a patient's home.

In U.S. patent Ser. No. 11/135,390, insights are provided to control an oxygen provider device based on patient's measurement data. There, an aim of such a control is to accurately determine a volume for high concentration oxygen as needed by a patient and adjust the volume dynamically based on the determination so to achieve a therapeutic effect. U.S. patent Ser. No. 11/135,390 is hereby incorporated by reference in its entirety.

In the present disclosure, another insight is that a timing of oxygen delivery to the patient can also be controlled here to reduce the aforementioned LPM gap for effective HFNC treatment in non-professional environment such as at a patient's home. For example, instead of providing oxygen continuously to the patient, in-home HFNC treatment in accordance with the present disclosure. During a HFNC treatment, a patient needs much more oxygen during an inspiration period of his/her breathing than an expiration period. Thus, the oxygen delivered to the patient in an HFNC treatment may consider this factor. Typically, the patient under the HFNC treatment has one or more underlying conditions to affect his/her lung as mentioned above. During the inspiration period, the patient is not able to obtain a normal amount of oxygen to sustain his/her basic functioning using his/her lung and thus needs assistance from an oxygen supply device to "push" the oxygen to the patient. Thus, in that period, oxygen should be supplied to the patient to fulfill the basic functioning needs of the patient, e.g., 40 LPM oxygen during that period is to be provided to the patient. On the other hand, during the expiration period, the patient exhales and may sustain even if there is no extra oxygen "pushed" to the patient at that point. Thus, during that period, the oxygen supply device may not provide oxygen to the patient.

Another insight provided by the present disclosure is that enriched oxygen supplied by the air separation unit in the integrated oxygen supply device can be blended with ambient air to achieve a desired FIO2 ration. This is because ambient air has around 21% oxygen, which can be blended with the enriched oxygen to be supplied to the patient. This further reduces the aforementioned LPM oxygen gap for an effective HFNC treatment.

In various embodiments, the integrated oxygen supply device in accordance with the present disclosure can include a compressor unit to compress ambient air for oxygen/nitrogen separation to produce oxygen enriched air. In another embodiments, the integrated oxygen supply device includes a compressor unit to compress the ambient air and a vacuum pump to remove the nitrogen enriched air from the device. The compression of the ambient air would generate heat. The compressor itself also generated heat during the operation. Traditionally the generated thermo energy is dissipated or controlled using a cooling mechanism such as an electrical fan. However, operation of the cooling mechanism means expenditure of energy to cool the compressor unit. Still another insight in accordance with the present disclosure is that, the heat generated by the compressor unit in those embodiments can be propagated through a heat exchange mechanism to heat gas delivered to the patient. In this way, the delivered gas is conditioned to a suitable temperature beneficial to the patient and the compressor unit is cooled by the heat exchange between the medium around the compressor unit and delivered air. This design can improve effectiveness of a treatment provided by an integrated oxygen supply device in accordance with the present disclosure, and as well as improve power consumption/efficiency of the integrated oxygen supply device in accordance with the present disclosure. In this way, power used to cool a compressor unit in an oxygen supply device and/or power used to heat gas to be delivered to the patient can be reduced or even eliminated. This can reduce form factor of the integrated oxygen supply device in accordance with the present disclosure, reduce manufacturing cost for the integrated oxygen supply device, improve affordability for in-home use of the integrated oxygen supply device, improve the life-time of the integrated oxygen supply device, long term reliability of the integrated oxygen supply device and improve safety for the integrated oxygen supply device.

Yet another insight provided by the present disclosure is that effectiveness of a treatment provided by an oxygen supply device can be different for different patients, or even different for the same patient at different stages of treatment phases. While the aforementioned 40/40 oxygen delivery may be an effective treatment for the patient while he or she has a severe condition such as the one under COVID-19, it may not be necessary after the patient has improved from the condition. In those phases, an assisted oxygen supply may be still used for the patient through the integrated oxygen supply device at a lower level of oxygen. Traditionally, for achieving the low level of oxygen, ambient air is injected to be blended with concentrated oxygen generated by an oxygen source. This, however, is unnecessary in many situations. In accordance with the present disclosure, a feature and/or control is provided to enable the integrated oxygen supply device in accordance with the present disclosure to be adjusted, either automatically or manually, to control the concentration level of oxygen generated by the integrated oxygen supply device so that no extra ambient air is injected to lower the oxygen concentration level for delivery to the patient. This provides flexibility to the integrated oxygen supply device to be adaptable to different treatments efficiently. This can reduce form factor of the integrated oxygen supply device in accordance with the present disclosure, reduce manufacturing cost for the integrated oxygen supply device, improve affordability for in-home use of the integrated oxygen supply device, improve a life-time of the integrated oxygen supply device, long term reliability of the integrated oxygen supply device and improve safety for the integrated oxygen supply device.

For achieving one or more of advantages mentioned above, in accordance with the present disclosure, an integrated oxygen supply device that is configured to generate oxygen continuously and release the oxygen non-continuously is provided. In some embodiments, the oxygen generated by the integrated oxygen supply device is stored in a porous material with the integrated oxygen supply device. The delivery of the oxygen produced by integrated oxygen supply device to a patient, in those embodiments, is controlled. In some embodiments, the control of the delivering oxygen is according one or more breathing patterns. The breathing pattern(s) may or may not be a current breathing pattern of the patient. For example, in one embodiment, the breathing pattern is a predetermined breathing pattern with a specified inspiration period followed by a specified expiration period. The specifications of the inspiration and expiration periods in the predetermined breathing pattern, in that embodiment, are configured to facilitate a 40 LPM oxygen supply to the user for the HFNC treatment.

In some embodiments, the integrated oxygen supply device in accordance with the present disclosure includes a heat exchange mechanism to enable heat exchange between a medium around a compressor unit employed by the integrated oxygen supply device and gas to be delivered to the patient. In some embodiments, the integrated oxygen supply device includes a control mechanism enabling adjustment of a concentration level of oxygen delivered by the integrated oxygen supply device to the patient. The adjustment in those embodiments can cause the integrated oxygen supply device to change one or more operations of how concentrate oxygen is generated and conditioned to be delivered to the patient.

In various embodiments, the integrated oxygen supply device comprises an air separation unit, a gas conditioning unit, a gas delivery unit, and/or any other components. In those embodiments, the air separation unit is configured to produce concentrated oxygen from ambient air. In one embodiment, the air separation unit comprises an oxygen concentration component configured to separate nitrogen from ambient air to obtain concentrated oxygen and stores the concentrated oxygen. In those embodiments, the stored concentrated oxygen is controlled to be released from the air separation unit according to a pulsing pattern. In various embodiments, the gas conditioning unit of the integrated oxygen supply device comprises a blending subunit, a compression subunit, a heating unit, a humidification unit and/or any other components. In various embodiments, the gas delivery unit is configured to deliver a high flow, high oxygen fraction, heated, humidified air to treated patients through a nasal canula. In one embodiment, the delivery of the air by the gas delivery unit is controlled according to a breathing pattern.

FIG. 1 illustrates generally an integrated oxygen supply device in accordance with the present disclosure. The integrated oxygen supply device 100 in FIG. 1 can use ambient air as an input gas and supply conditioned gas to a patient 102 for a treatment. Examples of the conditioned gas can include pressurized, high flow, heated, and/or humidified gas with a concentration level of oxygen. As mentioned above, an advantage of the integrated oxygen supply device 100 shown in FIG. 1 is that it is a single integrated device that can produce the conditioned gas to the patient 102 and can be used in a non-professional setting such as the patient 102's home due to its form factor and affordability for such a use.

Figure 2:
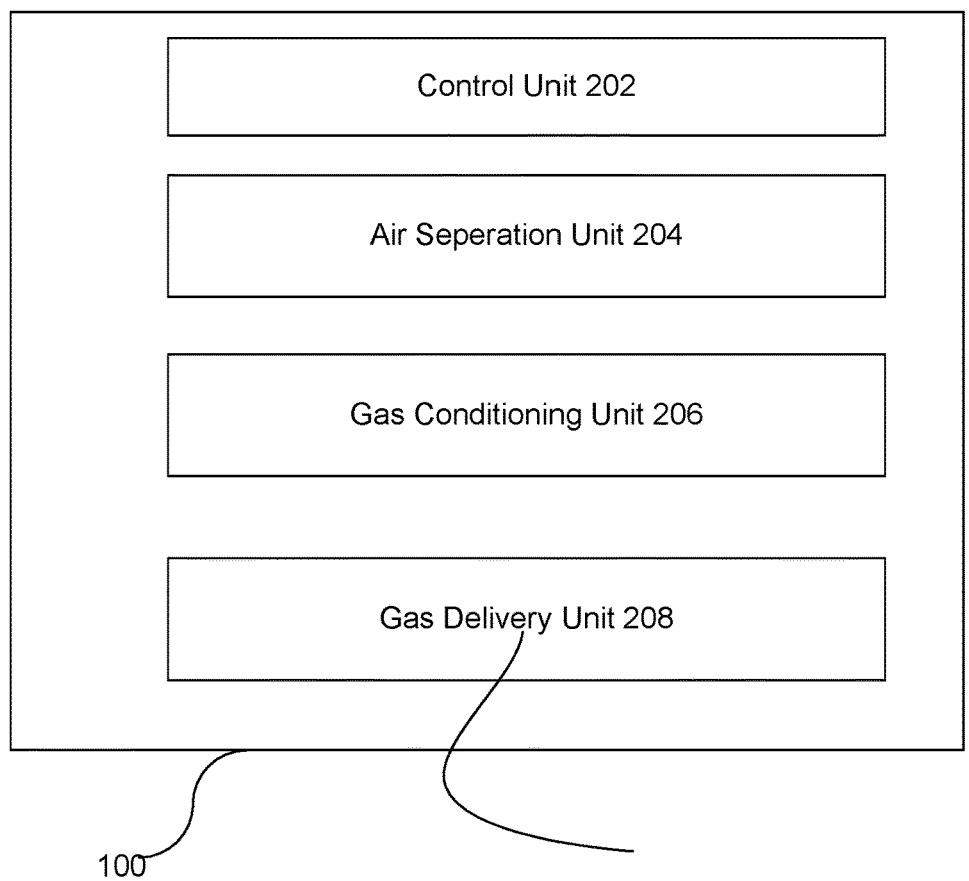
FIG. 2, illustrates an example an oxygen supply device shown in FIG. 1.

FIG. 2 illustrates an example of the integrated oxygen supply device shown in FIG. 1. As shown, in this example, the integrated oxygen supply device 100 includes a control unit 202, an air separation unit 204, an gas conditioning unit 206, an gas delivery unit 208, and/or any other components. The control unit 202 is configured to control various operations of the integrated oxygen supply device 100. In particular, control unit 202 in configured to control an oxygen release timing of the air separation unit 204, one or more conditions of conditioned gas generated by the gas conditioning unit 206, one or more operations of the gas conditioning unit 206, an oxygen delivery timing to the patient 102 by the gas conditioning unit 206, and/or any other aspects of the integrated oxygen supply device 100.

As will be appreciated by those skilled in the art, control unit 202, may be physically implemented using a software-controlled microprocessor, hard-wired logic circuits, or a combination thereof. For example, the control unit 202 may be implemented as a microprocessor configured to execute one or more software algorithms, including timing control, gas mixing control, gas conditioning processes of various embodiments described herein, in conjunction with a memory (not shown), to provide various functionalities of integrated oxygen supply device 100. That is, the control unit 202 may include a nonvolatile memory for storing executable software code that allows it to perform the various functions of integrated oxygen supply device 100 and various processes, discussed herein.

The air separation unit 204 is configured to receive ambient air, separate oxygen, and nitrogen in the received ambient air to produce concentrate oxygen, and output the concentrated oxygen. In various embodiments, the air separation unit 204 is controllable to store oxygen and output the concentrated oxygen upon a desired timing or Candance. In those embodiments, the air separation unit 204 is capable of outputting concentrated oxygen at a range between 40%-98% oxygen concentration.

The gas conditioning unit 206 is configured to receive the concentrated oxygen output by the air separation unit 204, and ambient air, and output conditioned gas using the received concentrated oxygen and ambient air. In various embodiments, the conditioned gas output by the gas conditioning unit 206 is conditioned by heating, humidifying, pressurizing and/or any other conditioning processes.

The gas delivery unit 208 is configured to receive conditioned gas and facilitate delivery of the received blended gas to the patient 102. In various embodiments, the gas delivery unit 208 is configured to facilitate the delivery of the received conditioned gas according to a pulsing pattern such that the blended gas is delivered to the patient in a controlled timing. It should be understood, not limited to a method where gas is delivered to the patient 102 based on the patient 102's inhale and exhale rhythm, the method employed by the gas delivery unit 208 can include a pulsing pattern predetermined for the patient 102. This can help the patient 102 adjust or adapt to a level desired for the patient 102. In addition, this can help improve oxygen LPM delivered to the patient 102 because the blended gas is not released to the patient 102 continuously.

Figure 3:
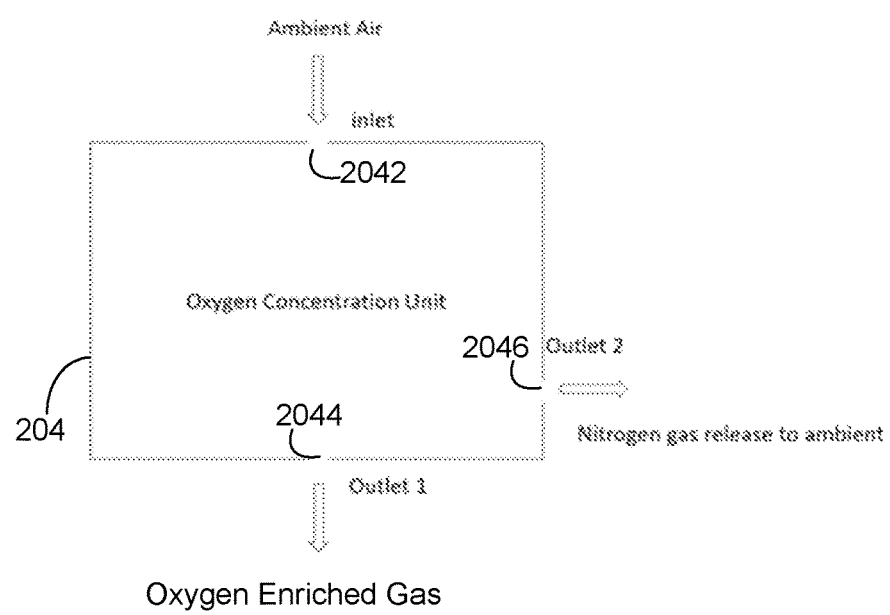
FIG. 3 illustrates an example of an air separation unit shown in FIG. 2.

With the integrated oxygen supply device 100 in accordance with the present disclosure having been generally described, attention is now directed to FIG. 3, where an example of an air separation unit 204 is illustrated. As can be seen, in this example, the air separation unit 204 comprises an inlet 2042, a first outlet 2044, a second outlet 2046 and/or any other components. First inlet 2042 is configured to receive ambient air from an environment where the integrated oxygen supply device 100 is located. The air separation unit 204 is configured to separate the oxygen and nitrogen in the ambient air received from the inlet 2042. In this example, the first inlet 2044 is configured to release oxygen enriched air (or concentrated oxygen) to the gas conditioning unit 206, and the second inlet 2046 is configured to release nitrogen enriched gas to the ambient air.

In some embodiments, the air separation unit 204 comprises a porous material, such as Zeolite, a MOF structure, a COF structure, and/or any other types of porous material. The porous material in those embodiments is employed to adsorb nitrogen from the ambient so to separate the oxygen from the nitrogen in the ambient air. In one embodiment, the nitrogen content in the ambient air is adsorbed when the ambient air flows through the porous material. In that embodiment, because the nitrogen content in the ambient air is adsorbed and released through the outlet 2046, enriched oxygen air or concentrated oxygen is obtained. In implementation, the release of adsorbed nitrogen can be controlled. For example, the adsorbed nitrogen is released when the porous material has reached a predetermined saturation level. In implementation, the release of the adsorbed nitrogen can be controlled by changing a pressure and/or temperature of the porous material.

In one implementation, the air separation unit 204 comprises an oxygen detector configured to detect a fraction of oxygen content in the oxygen enriched air around the first outlet 2044. In that implementation, the oxygen detector is arranged at the first outlet 2044. During a nitrogen adsorption phase of the air separation unit 204, a concentration level of the oxygen in the gas around first outlet 2044 is typically above 90%. When the porous material is being saturated, the concentration level of the oxygen in the air around first outlet 2044 starts to drop. In that implementation, a threshold level for the oxygen concentration level is preset, for example, in the control unit 202, such that when the concentration level of the oxygen detected by the oxygen detector is determined to be below the preset oxygen concentration level, the control unit 202 is configured to generate a control signal to control the first outlet 2044 to be closed and to control the second outlet 2046 to be open. This may be referred to as a nitrogen release phase of the air separation unit 204. In this phase, the nitrogen adsorbed by the porous material is released through the second outlet 2046 and the enriched oxygen air is stored around the first outlet 2044. As mentioned, in the nitrogen release phase, the adsorbed nitrogen can be released to the ambient air through the second outlet 2046.

Figure 4:
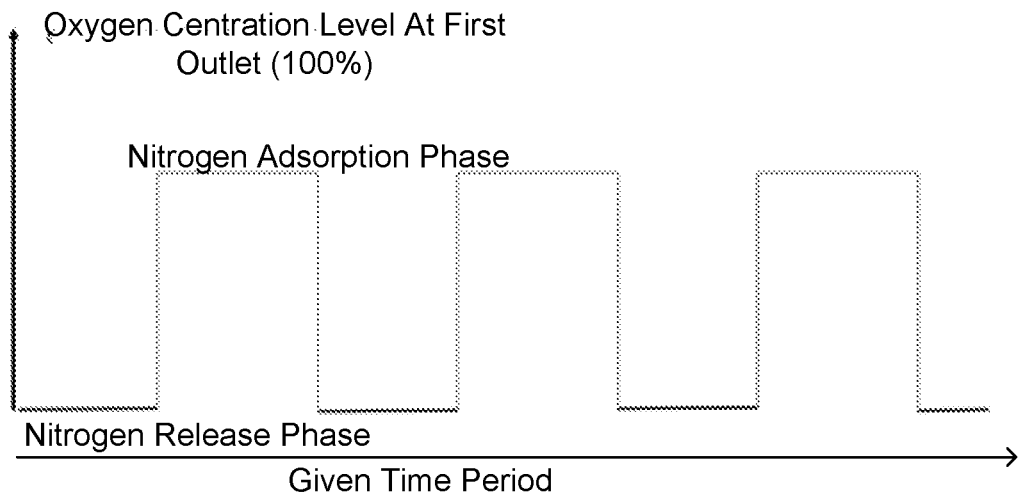
FIG. 4 illustrates one example of working states of the air separation unit shown in FIG. 2 in a given time period.

In some embodiments, the air separation unit 204 is configured to operate in at least two different modes—nitrogen adsorption phase and nitrogen release phase. In those embodiments, the air separation unit 204 is controlled to operate in a nitrogen adsorption phase immediately after a nitrogen release phase alternatively. FIG. 4 illustrates one example of working states of the air separation unit 204 in a given time period. As can be seen, in this example, the air separation unit 204 works in alternating nitrogen adsorption and release phases for corresponding sub-time-periods in the given time period. As illustrated, at the nitrogen release phase, the concentration level of the oxygen enriched air around first outlet 2044 is lower than the concentration level of the oxygen enriched air around first outlet 2044.

Figure 5:
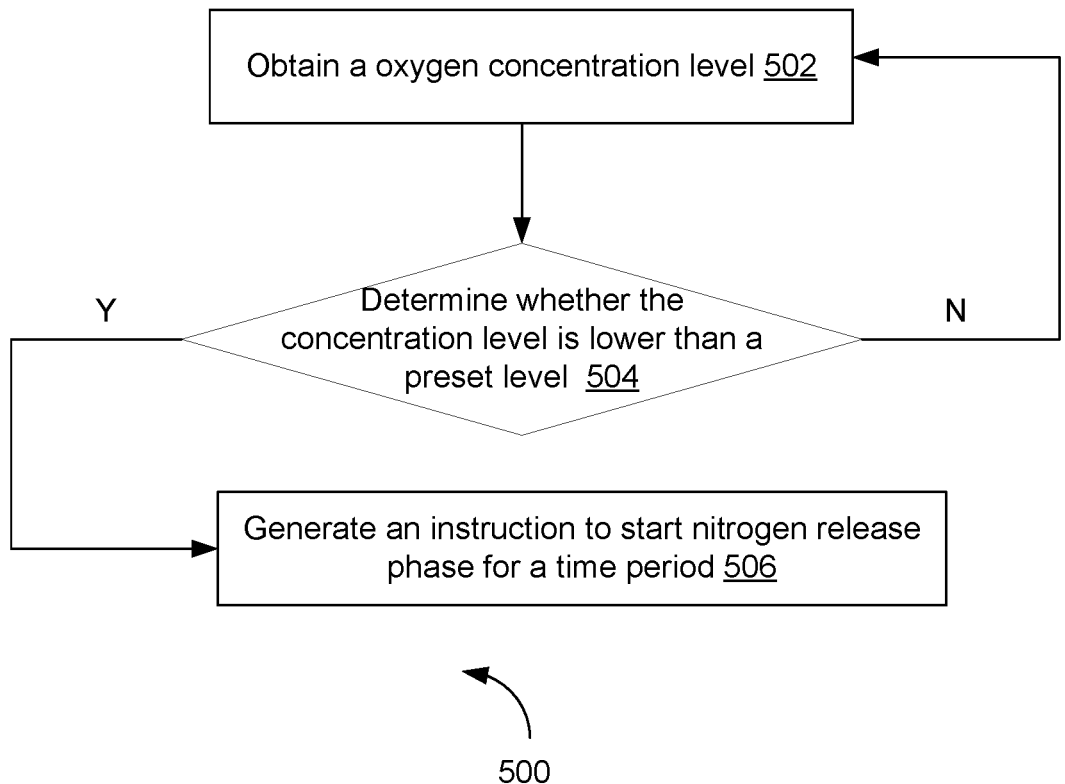
FIG. 5 illustrates one example of a method for controlling an operation of the air separation unit shown in FIG. 2 in accordance with the present disclosure.

In implementations, the control unit 202 can be employed to operate the air separation unit 204 in different modes. As mentioned above, the control unit 202 can be configured to obtain the concentration level of the oxygen enriched air around first outlet 2044 through the oxygen detector arrange there-about. FIG. 5 illustrates one example of a method 500 for controlling an operation of the air separation unit 204 in accordance with the present disclosure.

The operations of method 500 presented below are intended to be illustrative. In some embodiments, method 500 may be accomplished with one or more additional operations not described and/or without one or more of the operations discussed. Additionally, the order in which the operations of method 500 are illustrated in FIG. 5 and described below is not intended to be limiting.

In some embodiments, method 500 may be implemented by control unit 202 implemented by one or more of a processor, such as the ones shown in FIG. 2. The processor may include a digital processor, an analog processor, a digital circuit designed to process information, an analog circuit designed to process information, a state machine, and/or other mechanisms for electronically processing information. The control unit 202 may execute some or all of the operations of method 500 in response to instructions stored electronically on an electronic storage medium. The control unit 202 may include one or more components configured through hardware, firmware, and/or software to be designed for execution of one or more of the operations of method 500.

At 502, an oxygen concentration level around an outlet configured to release oxygen enriched air from an air separation unit is obtained. In some embodiments, as mentioned, an oxygen detector can be arranged around the outlet to detect the oxygen concentration level. In implementations, readings of the oxygen concentration level detected by the oxygen detector can be stored in a storage. The readings can be obtained at 502 from time to time.

At 504, a determination whether the oxygen concentration level obtained at 502 is lower than a threshold can be made. As mentioned, a threshold of 90%, for example, can be set. However, it should be understood, the threshold used at 504 can be a design choice such that it can be set to control the oxygen concentration level released from the air separation unit 204. A higher concentrate level would need a higher threshold and vice versa. The higher threshold would mean more frequent alternating between the nitrogen adsorption and release phases shown in FIG. 4. That may decrease an overall lifetime of the air separation unit. However, on the other hand, higher oxygen concentration level would mean better oxygen enriched air supply to the gas conditioning unit. In one implementation, the threshold used at 504 is adjustable by an operator. In that implementation an interface is provided facilitate the operator to adjust the threshold to control the oxygen concentration level of the oxygen enriched air released by the air separation unit.

In some embodiments, the threshold level at 504 can be dynamically adjusted through an interface provided by the integrated oxygen supply device. For example, the interface may be configured to enable an operator of the integrated oxygen supply device to select a preset oxygen supply mode, which may correspond to a range of oxygen concentration level in the enriched oxygen air. For example, an oxygen supply mode corresponding to an oxygen concentration level between 25%-30% may be provided to assist the patient breathe. As will be described, this can help improve an efficiency and power consumption of the integrated oxygen supply device.

As can be seen, in this example, when the determination at 504 is that the oxygen concentration level is not lower than the threshold, the method flows back to 502 to obtain the oxygen concentration level again for the next determination 504 until the determination at 504 is that the oxygen concentration level is lower than the threshold, and then the method proceeds to 506.

At 506, an instruction is generated to start the nitrogen release phase for a time period. For example, a predetermined time period may be employed for 506. In implementation, this time period can be obtained from experimentations or specification for the porous material to release the adsorbed nitrogen until a nitrogen saturation level in the porous material is lower than a desired level. The instruction generated at 506 can cause a pressure and/or temperature change to the porous material so to trigger the porous material to release the adsorbed nitrogen. The instruction at 506 can cause an outlet such as the first outlet 2044 to be closed and another outlet such as the outlet 2046 to be opened for the time period. This can facilitate the adsorbed nitrogen to be released through the second outlet 2046 and the oxygen enriched air to be stored around the first inlet 2044.

In implementations, multiple air separation units can be employed to increase an oxygen production of the integrated oxygen supply device. For example, the integrated oxygen supply device 100 may include 2 air separation units 204 to double the oxygen supply to the gas conditioning unit 206. This can improve oxygen LPM for a treatment performed by the integrated oxygen supply device.

In implementations, the air separation unit 204 can include multiple subunits. Each subunit can contain porous material configured to adsorb nitrogen gas. In operation, one or more of the subunit can be arranged to work at the same time. In those implementations, when a given subunit is in an operational mode, ambient air is injected to the given subunit to cause the nitrogen content in the ambient air to be adsorbed when the ambient air flows through the porous material in the given subunit. As explained above, this results in oxygen enriched air to be generated and stored. When porous material in the given subunit is saturated with adsorbed nitrogen, the given subunit is controlled to be swapped out of the operational mode. This control can be achieved by the control unit 202. As mentioned above, one way of determining whether the given subunit is saturated over a predetermined level is to detect concentration level of oxygen around an outlet where the concentrated oxygen is released. As the porous material is being saturated, its effectiveness to adsorb nitrogen reduces to cause the oxygen concentration level to drop. Once the given subunit is put in the non-operational mode, it can be controlled to release the adsorbed nitrogen to the environment where the integrated oxygen supply device is located.

When the given subunit is swapped out of the operation, another subunit can be controlled to be swapped into the operation. This involves injecting the ambient air into that subunit. In this way, different subunits work in alternating patterns. The ambient air is first injected into a first subunit to produce oxygen concentrated air. When the porous material in the first subunit is saturated with nitrogen, the ambient air injection is moved from the first subunit to a second subunit to produce oxygen concentrated air, while the porous material in the first subunit is heated to remove and release nitrogen. A method for controlling the air separation unit having multiple subunits to work in such an alternative pattern can be implemented in the control unit 202.

Figure 6:
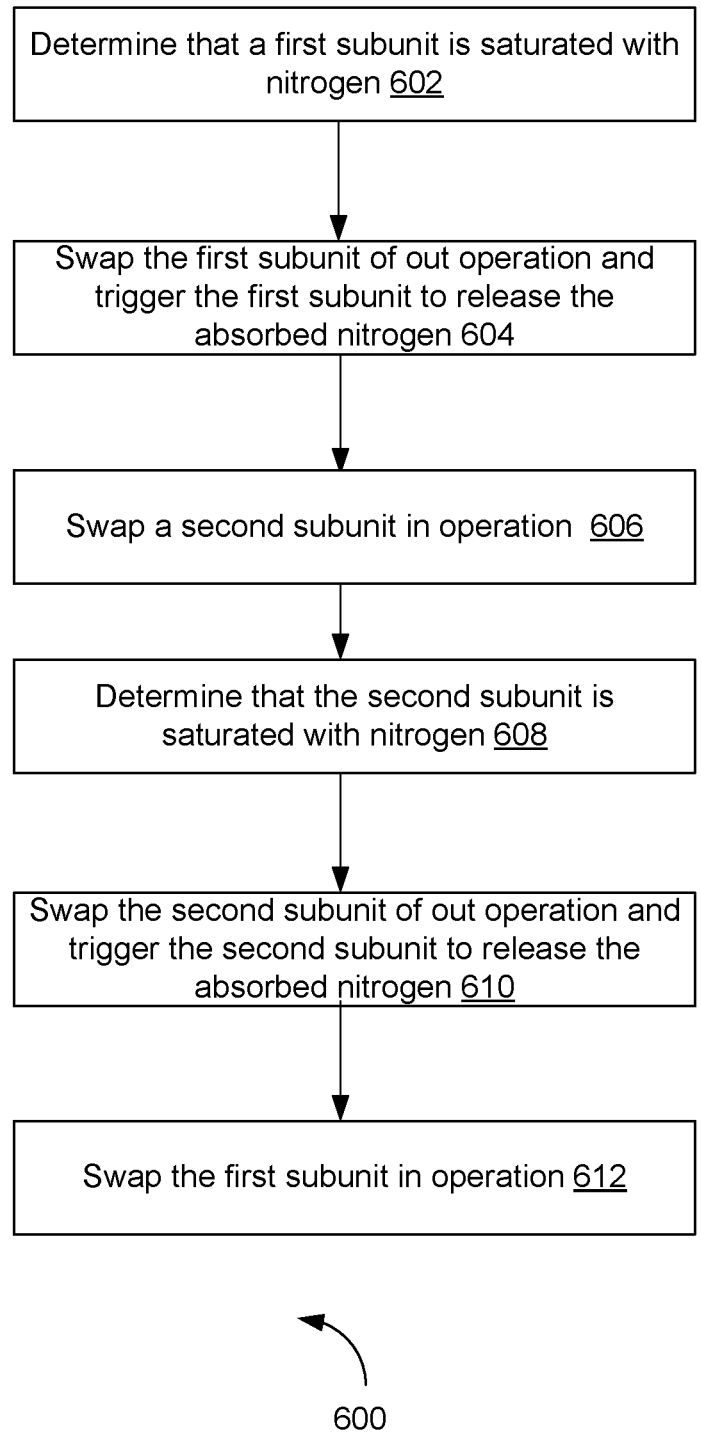
FIG. 6 illustrates one example method for controlling multiple subunits in an air separation unit shown in FIG. 2 in accordance with the present disclosure

FIG. 6 illustrates one example method 600 for controlling multiple subunits in an air separation unit in an integrated oxygen supply device in accordance with the present disclosure. The operations of method 600 presented below are intended to be illustrative. In some embodiments, method 600 may be accomplished with one or more additional operations not described and/or without one or more of the operations discussed. Additionally, the order in which the operations of method 600 are illustrated in FIG. 6 is not intended to be limiting.

In some embodiments, method 600 may be implemented by a control unit 202 implemented by one or more of a processor, such as the ones shown in FIG. 2. The processor may include a digital processor, an analog processor, a digital circuit designed to process information, an analog circuit designed to process information, a state machine, and/or other mechanisms for electronically processing information. The control unit 202 may execute some or all of the operations of method 600 in response to instructions stored electronically on an electronic storage medium. The control unit 202 may include one or more components configured through hardware, firmware, and/or software to be designed for execution of one or more of the operations of method 600.

Figure 7:
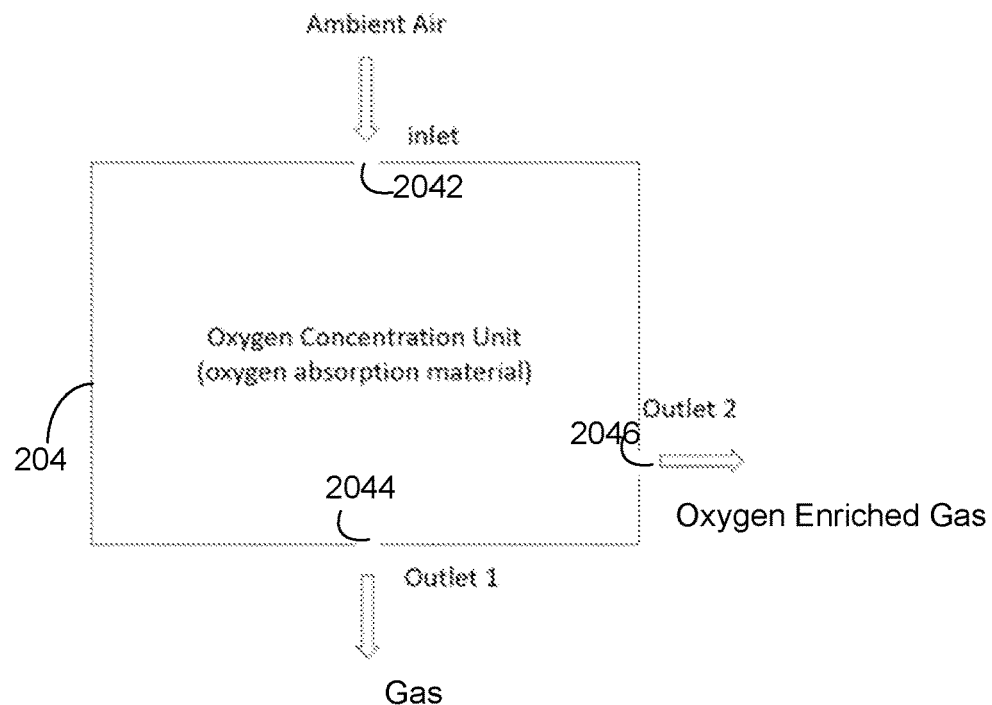
FIG. 7 illustrates another example implementation of air separation unit shown in FIG. 2 in accordance with the present disclosure.

In some embodiments, the air separation unit 204 includes a porous material, such as specially designed MOF and COF structure, which adsorbs oxygen. Nitrogen enriched air through the porous material, in those embodiments, is released to the ambient air. Oxygen gas adsorbed by the porous material is then released by change of temperature or pressure. The released oxygen is collected by the oxygen storage unit. MOF and COF structure with special design can contain surface area per volume significantly larger than natural zeolite materials. In addition, the oxygen content in the air is 4 times less than the nitrogen content in the same volume of the air. As a result, these embodiments can significantly increase the production of oxygen enriched air in unit time and unit volume per adsorption material. FIG. 7 illustrates an example implementation of air separation unit 204 configured with MOF/COF. As can be seen, comparing with the example air separation unit 204 shown in FIG. 3, the outlet 2044 in this example is configured to release nitrogen enriched air and the outlet 2046 is configured to release adsorbed oxygen.

Figure 8:
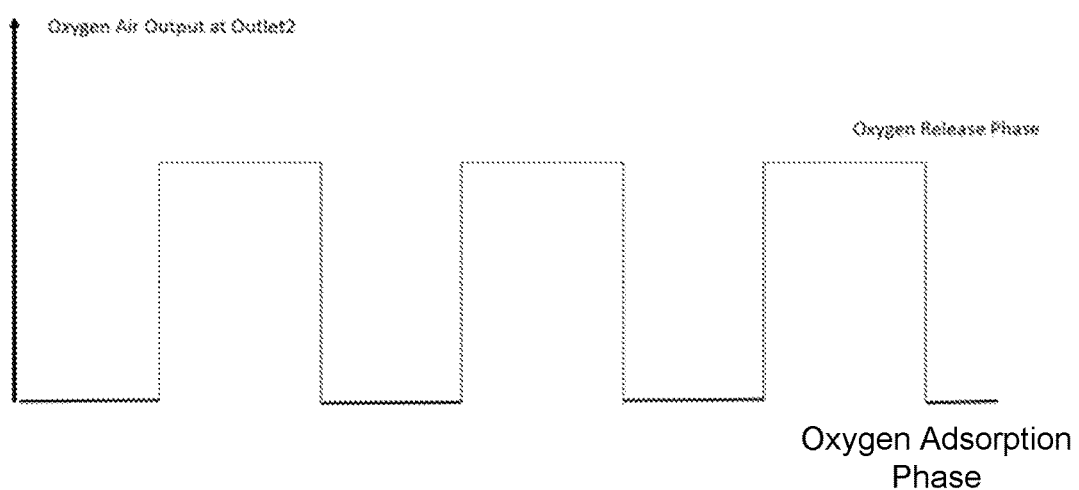
FIG. 8 illustrates one example of working states of the air separation unit shown in FIG. 7 in a given time period.

FIG. 8 illustrates one example of working states of the air separation unit 204 in each time period, where the air separation unit 204 in this example has MOF/COF. As can be seen, in this example, the operation modes of the air separation unit 204 include oxygen release and adsorption phases. As also can be seen, in this example, the oxygen concentration level is detected at outlet 2046 shown in FIG. 7.

In some embodiments, the air separation unit 204 includes multiple subunits configured to adsorb oxygen gas from ambient air. In those embodiments, the multiple subunits are controlled to work in subsets alternatively. For example, a subset of two subunits are arranged to work in a first time period and another subset of two other subunits are arranged to work in a second time period. In those embodiments, the oxygen content in the injected ambient air is adsorbed when air flow through the porous material, resulting in oxygen air to be stored. When porous material in the subunit is saturated with oxygen gas, the oxygen gas is released by changing temperature and/or pressure of the subunit. The released oxygen gas is stored or delivered to the gas conditioning unit 206. Different subunits work in alternating patterns. The ambient air is first injected into the first subunit, oxygen is adsorbed and stored on the surface of the porous materials. When the porous material in the first subunit is saturated with oxygen, the ambient air injection is moved from the first subunit to the second subunit, while the porous material in the first subunit is heated to remove and release oxygen to storage or to be delivered to the gas conditioning unit 208.

Figure 9:
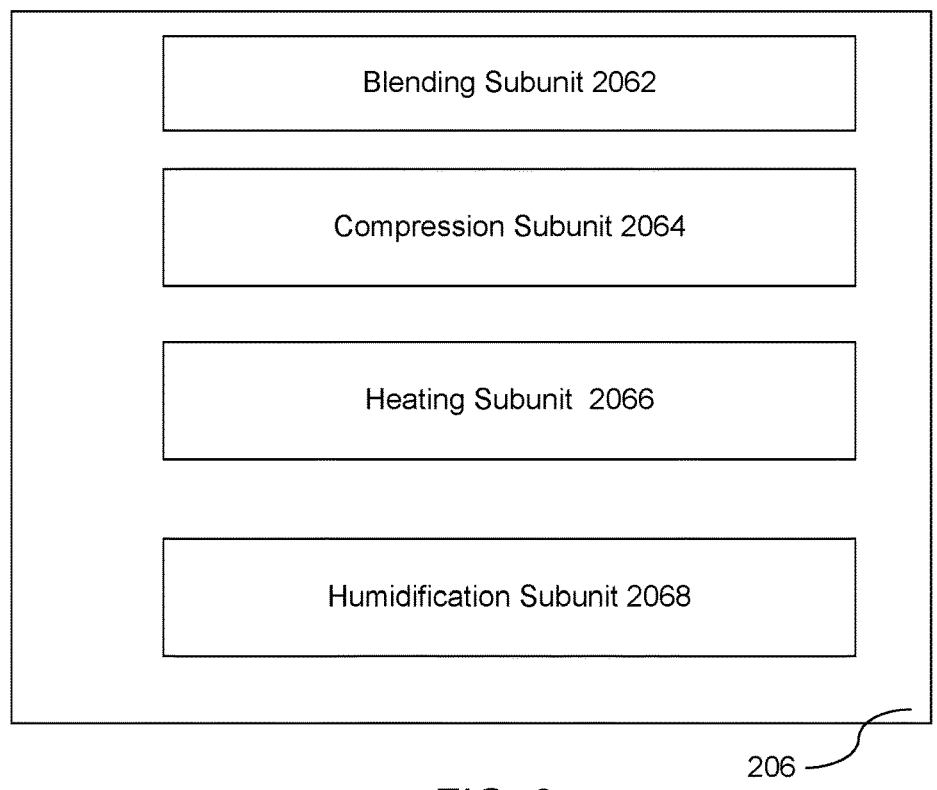
FIG. 9 illustrate an example of the gas conditioning unit shown in FIG. 2.

Attention is now directed back to FIG. 2. In various embodiments, the gas conditioning unit 206 contains a blending subunit 2062, a compression subunit 2064, a heating unit 2066, a humidification unit 2068, and/or any other components. FIG. 9 illustrate an example of the gas conditioning unit 206.

Figure 10:
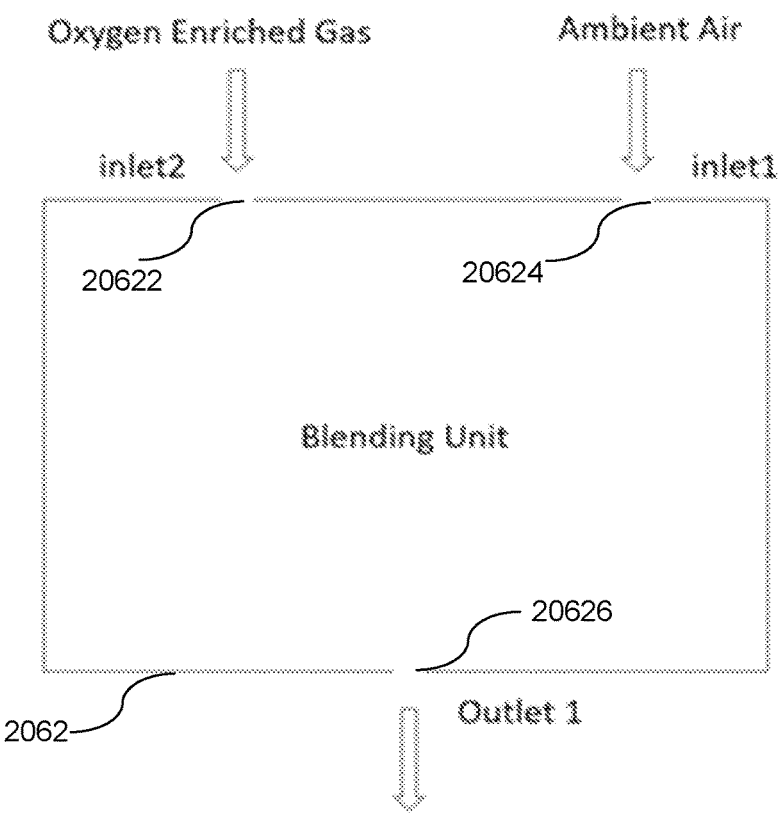
FIG. 10 illustrates an example of a blending subunit shown in FIG. 9.

The blending subunit 2062 is configured to combine ambient air with oxygen enriched gas produced by the air separation unit 204 at a desired ratio. FIG. 10 illustrates an example of a blending subunit 2062. As can be seen, in this example, there are two inlets to the blending subunit 2062, namely inlet 20622 and inlet 20624. In this example, the ambient air is inputted through inlet 20624, and the oxygen enriched gas from the air separation unit 204 is inputted through inlet 20622. The blended gas generated by the blending subunit is outputted through outlet 20626 to the compression subunit 2064. The desired ratio may be determined to achieve a final oxygen fraction delivered to the patient 102. In one embodiment, It the desired ration is determined by the patient physiological profile and treatment requirement.

Figure 11:
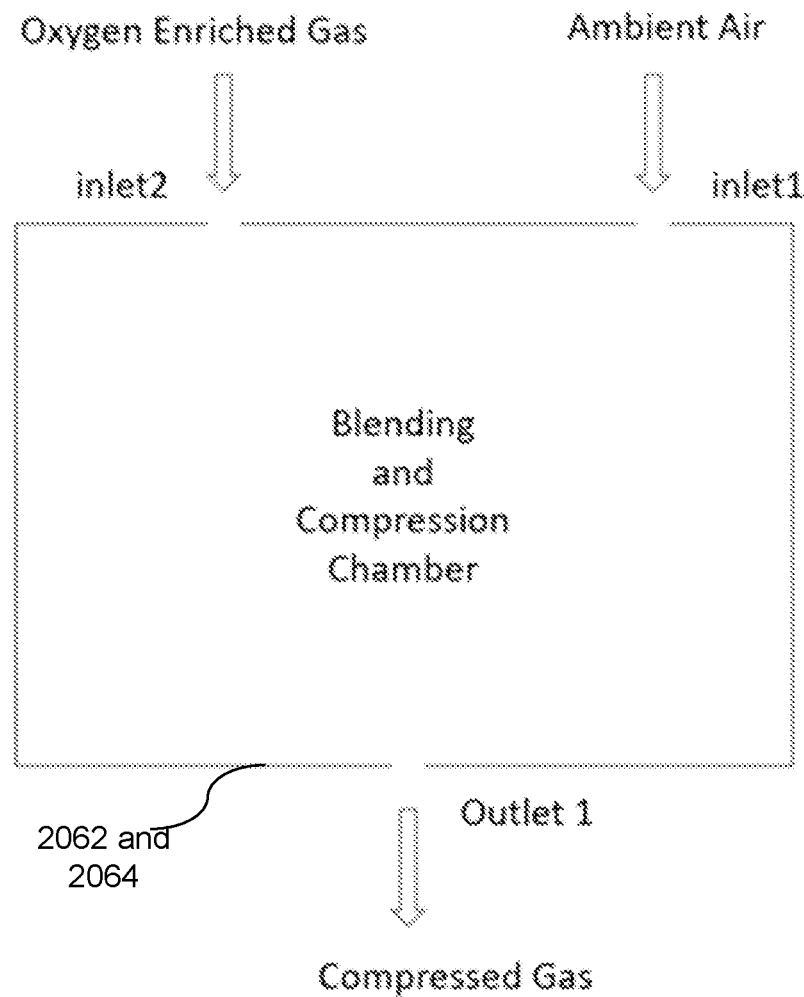
FIG. 11 illustrates another example of the blending subunit and compression subunit shown in FIG. 9.

The compression subunit 2064 is configured to receive blended air from the blending subunit 2062 from the outlet 20626, compress the blended air to achieve a desired pressure and/or flow rate. In implementation, pressure sensors and flow sensors can be applied in the compression subunit 2064 to detect whether pressure and flow rate of the blend air has reached the desired level. Feedback control mechanisms can be applied in the compression subunit 2064 to ensure the desired pressure and flow rate is achieved. In one embodiment, the desired flow rate is determined by the patient physiological profile and treatment requirement. In one embodiment, the blending subunit 2062 and the compression subunit 2064 can share the same blender gas chamber, as shown in FIG. 11.

The heating subunit 2066 is configured to heat the compressed gas from the compression subunit 2064 to a desired temperature point. The temperature of the inhaled gas by patient 102 impacts the comfort level of the patient 102 and subsequently the compliance of the treatment. The inhaled gas temperature also impacts the physiological response of the patient 102's respiratory system. The gas temperature impacts an achievable humidification level of the inhaled gas, which subsequently impacts the treatment effectiveness and potential side effect of the treatment. Thus, accurate temperature control is important to ensure that the temperature of the inhaled gas at the nasal canula. Typically, the temperature of the inhaled gas to a patient is set at 37 degrees or slightly lower, supported by prior clinical studies.

The humidification subunit 2068 is configured to humidify the heated compressed gas from the heating subunit 2066. Normally, the upper respiratory tract of a healthy person humidifies the inhaled air to saturation level at body temperature, which is close to 37 degrees Celsius (37° C.). If natural respiratory humidification fails, pulmonic infections and damage to lung tissue may be the consequence. The appropriate humidification level is essential for the healthy functioning of the human respiratory system and effective treatment of the breathing machine. Since the flow rate of the invented breathing device is significantly larger than the normal inspiration flow rate accustomed to the human respiratory system, the natural respiratory system may not be able to provide sufficient humidification needed. Thus, it is essential to elevate the humidity level of the heated gas to alleviate the burden to the human respiratory system when using the breathing machine.

In various embodiments, the added humidity and heat to the blended gas by the gas conditioning unit 206 makes inhaled gas delivered to the patient 102 more palatable, especially at a higher flow rate. The most effective humidification is the pass-through type humidification, in which the gas pass on top heated water, and additional water vapor is added and the gas is also heated by thermo energy transferred from the warm water. An electrical heating electrical heating element is used to heat up water and a closed-loop temperature/humidity control is employed. The process is energy hungry, due to the thermo energy dissipating and loss in the head conductivity. In one embodiment, a heated water reservoir is applied as the humidification subunit 2068 and the heating subunit 2066 in the integrated oxygen supply device 100. In that embodiment, the temperature of the reservoir is set at a pre-determined value, based on the temperature humidity lookup table.

In another embodiment, temperature sensors and humidity sensors are arranged detect the temperature and humidity of the inhaled gas at or near a nasal canula to the patient 102. In that embodiment, feedback control mechanism is applied in the control unit 202 to control the heating subunit 2066 and humidification subunit 2068 to ensure achievement of the desired temperature and humidity levels of the inhaled gas at the nasal canula.

Figure 12:
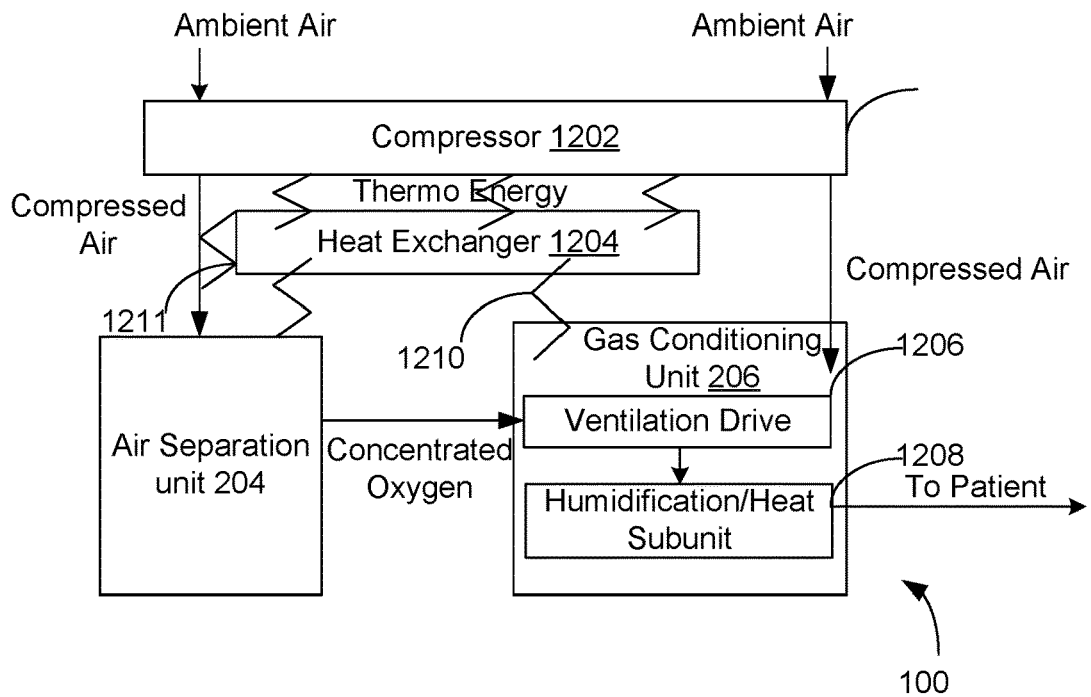
FIG. 12 illustrate another example of integrated oxygen supply device shown in FIG. 1 showing various components of the integrated oxygen supply device.

In various embodiments, integrated oxygen supply device 100 includes a compressor configured to compress ambient air for provision to the air separation unit 204 and/or the gas conditioning unit 206. FIG. 12 illustrates one example of such an integrated oxygen supply device 100. As can be seen, in this example, the compressor 1202 is arranged upstream of the air separation unit 204 and the gas conditioning unit 206 in terms of ambient air flow. The compressor 1202 is configured to compress ambient air such that compressed ambient air is supplied to the air separation unit 204 and/or to the gas conditioning unit 206. As can be seen, as the ambient air being compressed by the compressor 1202, thermo energy is generated when the pressure in the ambient air is increased. In a traditional oxygen concentration process, an electrical fan is typically used to cool the compressor 1202 and its surrounding medium to avoid overheating of the compressor 1202.

However, as mentioned above, the thermo energy generated by the compressor 1202 can be employed to condition the gas to be delivered to the patient. That is, heating the gas would need heat source. Thus, one design of the integrated oxygen supply device, as shown in FIG. 12, is to use the thermo energy generated by the compressor 1202 to heat the gas to be delivered to the patient. For achieving this, in this example, a heat exchanger 1204 is arranged between the compressor 1202, and the air separation unit 204 and the gas conditioning unit 206. In implementation, the heat exchanger 1204 can include air guides or channels to facilitate heat exchange between a medium surrounding the compressor 1202, compressed air 1211, concentrated oxygen generated by the air separation unit 204 and gas conditioning unit 206.

In this example, the gas conditioning unit 206 comprises a ventilation drive 1206 and a humidification/heat subunit 1208. As can be seen, in this example, the concentrated oxygen generated by the air separation unit 204 can be supplied via heat communication 1210 to the ventilation drive 1206 for blending with the compressed ambient air, and/or to the humidification/heat subunit 1208 for conditioning. The heat communication can be implemented using a heat conductor such as water line made of metal pieces. The water line in that implementation contains water that is heated during the heat exchange around heat exchanger 1204. The heat absorb by the water in the water line is transmitted to the ventilation drive and/or humidification/heat subunit to heat the gas to be delivered to the patient.

The heat exchanger 1204 can be arranged and configured to facilitate heat exchange between the medium around compressor 1202 and the concentrated oxygen as a cooling mechanism for the compressor 1202 and a heat source for heating the concentrated oxygen from the air separation unit 204. In this way, a power consumption for the integrated oxygen supply device is reduced because the power used to operate the compressor 1202 is also employed, indirectly, for heating the gas to be delivered to the patient, and the compressor is cooled without extra power by employing additional cooling mechanism such as an electrical fan. This can improve form factor of the integrated oxygen supply device in accordance with the present disclosure, reduce manufacturing cost for the integrated oxygen supply device, improve affordability for in-home use of the integrated oxygen supply device, improve a life-time of the integrated oxygen supply device, long term reliability of the integrated oxygen supply device and improve safety for the integrated oxygen supply device.

In some embodiments, the ambient air is not compressed by the compressor 1202 for blending with the concentrated oxygen produced by the air separation unit 204. In those embodiments, the compressor 1202 is employed in a path where compressed ambient air is injected into an inlet of the air separation unit 204 such as the inlet 2042 shown in FIG. 2. In those embodiments, compression of the ambient air can increase a PSA of the ambient air so to increase separation efficiency of the air separation unit 204. As will be described, the compressor 1202 can be controlled to adjust a compression level of the ambient air to be injected into the inlet 2042. This can reduce form factor of the integrated oxygen supply device in accordance with the present disclosure, reduce manufacturing cost for the integrated oxygen supply device, improve affordability for in-home use of the integrated oxygen supply device, improve a life-time of the integrated oxygen supply device, long term reliability of the integrated oxygen supply device and improve safety for the integrated oxygen supply device.

Figure 13:
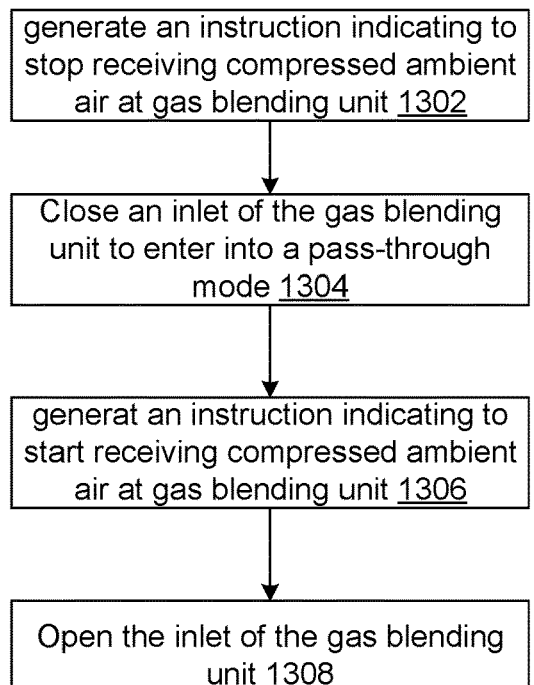
FIG. 13 illustrates a method for controlling the integrated oxygen supply device shown in FIG. 12.

FIG. 13 illustrates an example of a method for controlling the integrated oxygen supply device shown in FIG. 12. In various embodiments, the method 1300 shown in FIG. 3 is implemented by control unit 202 shown in FIG. 2. As can be seen, in this example, instruction can be generated stop or start receiving ambient air at the gas conditioning unit 206 shown in FIG. 2. After the instruction to stop receiving the ambient air is generated, the control unit 202 is configured to execute the instruction by closing off an inlet of the gas conditioning unit 206, for example inlet 20624 shown in FIG. 10. In this way, the gas conditioning unit 206 is controlled to be working in a pass-through mode such that concentrated oxygen produced by the air separation unit 204 is passed into gas conditioning unit 206 for conditioning (such as heating or humidifying) without being blended with ambient air. As mentioned, this mode can be useful when the treatment to the patient 102 does not need relatively high concentration level of the oxygen. As described above, the air separation unit 204 in some embodiments can be controlled to produce relatively lower concentrated level of oxygen. For example, in a situation, where the patient merely needs some sort of oxygen assistance (as compared to precise 40/40 high flow oxygen assistance), this mode can be turned on. In this way, a power usage is reduced for the integrated oxygen supply device because no power is needed to blend the ambient air with highly concentrated oxygen to reach relatively low concentration level of oxygen to be delivered to the patient. Thus, this mode can improve an efficiency of the integrated oxygen supply device in those embodiments. —add feedback control of compressor based on troutput flow rate and oxygen fraction at the patient.

Attention is once again directed back to FIG. 2. The gas delivery unit 208 is configured to deliver the high flow, high oxygen fraction, heated, humidified air to patient 102 through a nasal canula. In one embodiment, a gas tubing connects a nasal canula to an outlet of the gas conditioning unit 206. In that embodiment, the tubing is heated to ensure temperature and humidity of inhaled gas to though at the nasal canula point. In that embodiment, temperature sensors and humidity sensors are applied on the gas tubing to monitor the temperature and humidity of the delivered gas. In that embodiment, feedback control mechanism are implemented in the control unit 202 to ensure control of the temperature and humidity, and delivery of the high flow oxygen enriched gas to the patient 102 at the proper temperature and humidity.

As mentioned above, conventional HFNC device used in hospitals provide a constant flow of oxygen enriched gas to patients. In various embodiment, as mentioned, the integrated oxygen supply device 100 includes an air separation unit 204 in place of the oxygen tanks or oxygen supply from a central oxygen generator commonly used in the hospital setting. In one embodiment, the integrated oxygen supply device is configured to deliver high oxygen fraction, high flow, heated and humidified air to patient 102 at pre-determined constant flow rate and constant oxygen fraction. This delivery model is like the conventional HFNC model being applied in the hospitals.

It is sometimes desirable to limit the size of the integrated oxygen supply device for mobility needs. This size limit may limit the size of the porous material being used in air separation unit 204, and/or the number of oxygen concentration subunits included in the air separation unit 204, which in turn may limit the oxygen supply to meet the requirement of when ultra-high flow rate and high oxygen fraction for an effective treatment. A conventional HFNC machine typically provides a same level of oxygen flow to a patient when the patient is expiration, when oxygen is only needed during the patient's inspiration phase.

Figure 14:
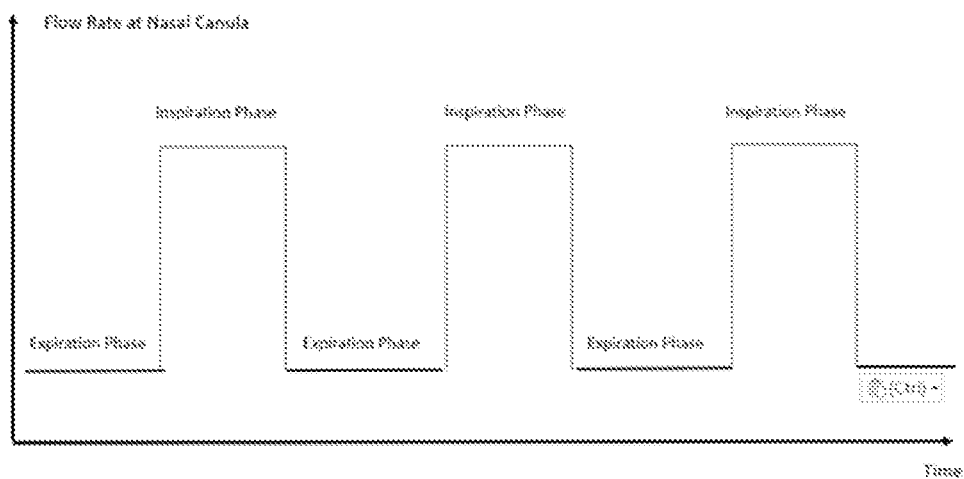
FIG. 14 illustrates an example of relationship of a flow rate of oxygen delivered by the gas delivery unit shown in FIG. 2 to the patient with patient's inspiration and expiration phases.

In various embodiment, the gas delivery unit 208 is configured to be controlled to deliver conditioned oxygen according to a predetermined pattern to avoid waste of oxygen during patient's expiration phase, and at the same time meet the treatment and respiratory support requirement to the patients during the inspiration phase. FIG. 14 illustrates an example of relationship of a flow rate of oxygen delivered to the patient 102 with patient's inspiration and expiration phases. As can be seen, oxygen is delivered to the patient 102 at a higher flow rate during the inspiration phases of the patient 102 than the expiration phases of the patient 102.

As mentioned, the predetermined delivery pattern of the gas delivery unit 208 can be controlled by the control unit 202 and can be set according to an oxygen delivery consideration, such as the amount of oxygen needed for a treatment to the patient. In various embodiments, an interface is provided on the integrated oxygen supply device 100 to enable an operator to adjust a timing of delivering the oxygen through the gas delivery unit 208. In those embodiments, the predetermined delivery pattern is thus adjustable. This can help the operator to train the patient 102 to adjust or adapt to a breathing condition appropriate for the patient 102.

In one embodiment, the oxygen delivery pattern works in the following way: when a patient inhales, the flow rate at a nasal canula of the gas delivery unit 208 increases to a desired level. When the patient exhales, the flow rate at the nasal canula decreases to a basic level which can be the lowest level supported by the integrated oxygen supply device 100. In that embodiment, respiratory sensors is used to detect the breathing cycle of the patient. In that embodiment, the control unit 202 is configured with algorithms to control the gas conditioning unit 206 and the gas delivery unit 208 to synchronize the flow pulse timing to the breathing cycle of the patient 102.

Figure 15:
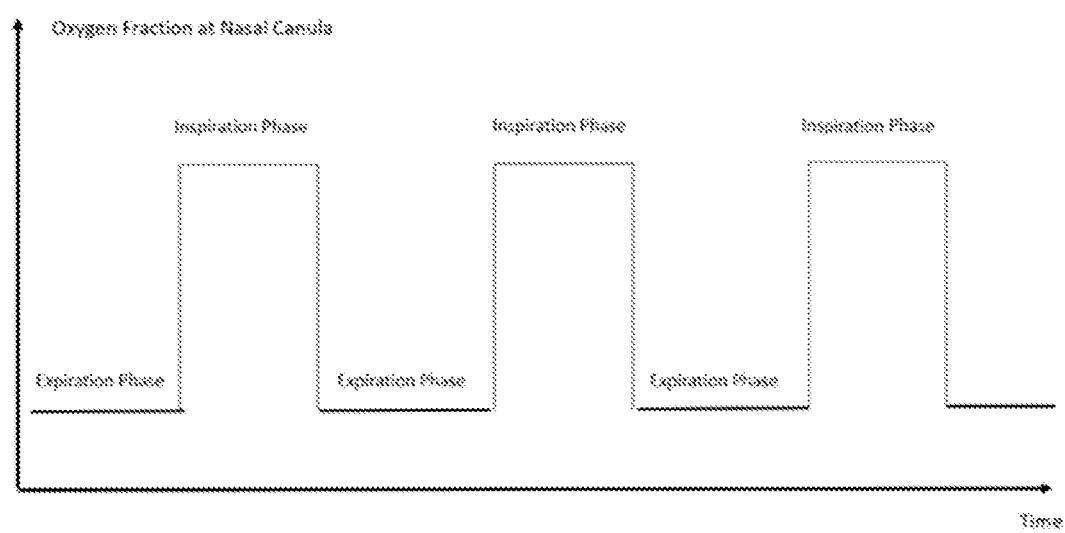
FIG. 15 illustrates an example of a relationship between oxygen fraction at the nasal canula and patient's inspiration and expiration phases in that embodiment.

In another embodiment, the gas delivery unit 208 is configured to operate in a pulsed mode at a pre-determined rate and time sequence, instead of synchronizing to the natural breathing cycle of the patients. Under this pulsing mode, the patient's breathing cycle is entrained to synchronize with the pre-determined pulsing rate and timing provided by the integrated oxygen supply device 100. In another embodiment, the flow rate of provided by the delivery unit 206, whilst the oxygen fraction of the delivered gas varies in pulsing mode. This is achieved by controlling the flow rate of the oxygen enriched gas flow through the inlet 2064 of the blending subunit 206 shown in FIG. 9. FIG. 15 illustrates an example of a relationship between oxygen fraction at the nasal canula and patient 102's inspiration and expiration phases in that embodiment.

Figure 16:
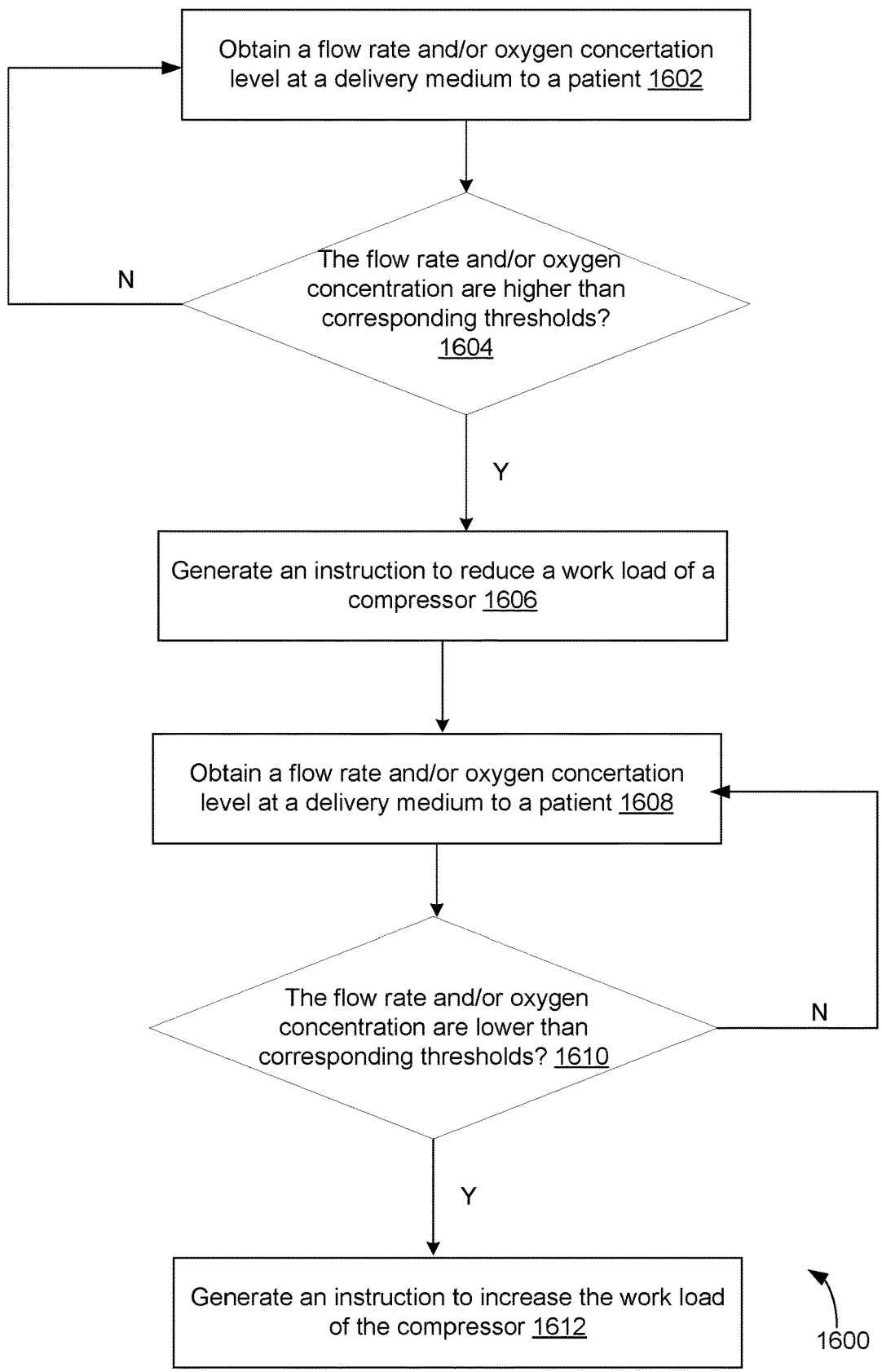
FIG. 16 illustrate a method for controlling a workload of a compressor in the integrated oxygen supply device shown in FIG. 12.

FIG. 16 illustrates a method 1600 for controlling a compressor in the integrated oxygen supply device for achieving desired oxygen flow rate and/or concentration level at a delivery end of the patient. Method 1600 can be implemented by control unit 202 shown in FIG. 2. As shown, in this method, a feedback loop is employed to control the compressor such as the compressor 1202 shown in FIG. 12. The feed loop involves obtaining a flow rate and/or oxygen concentration level of the gas delivered to the patient. For example, sensors can be installed in the nasal canula to detect such. The obtained flow rate and/or oxygen concentration level is then compared with corresponding thresholds. For example, a threshold for a recovery treatment mode may be set such that the flow rate and/or the oxygen concentration level are lower than another threshold for an active treatment. For example, when the obtained flow rate and/or oxygen concentration level is higher than the recovery treatment threshold, this means gas delivered to the user may not be necessary in terms of its flow rate and/or oxygen concentration. Once that is determined, the control unit 202 can generate an instruction to reduce a workload of the compressor 1202 so to decrease a PSA of the ambient air injected into the air separation unit 204. This in turn causes the separation of oxygen and nitrogen to drop in terms of an oxygen concentration level produced by the air separation unit 204, which may be sufficient for the recovery treatment. As also shown, the control unit 202 can also be configured to determine whether the obtained flow rate and/or oxygen concentration level is lower than a threshold. For example, the integrated oxygen supply device 100 can be transitioned from recovery treatment to an active treatment. In that transition, the compressor 1202 would need to be geared up to increase the PSA of the ambient air injected into air separation unit 204. This design can improve efficiency of the integrated oxygen supply device in accordance with the present disclosure, reduce manufacturing cost for the integrated oxygen supply device, improve affordability for in-home use of the integrated oxygen supply device, improve a life-time of the integrated oxygen supply device, long term reliability of the integrated oxygen supply device and improve safety for the integrated oxygen supply device.

Example Computer System

Figure 17:
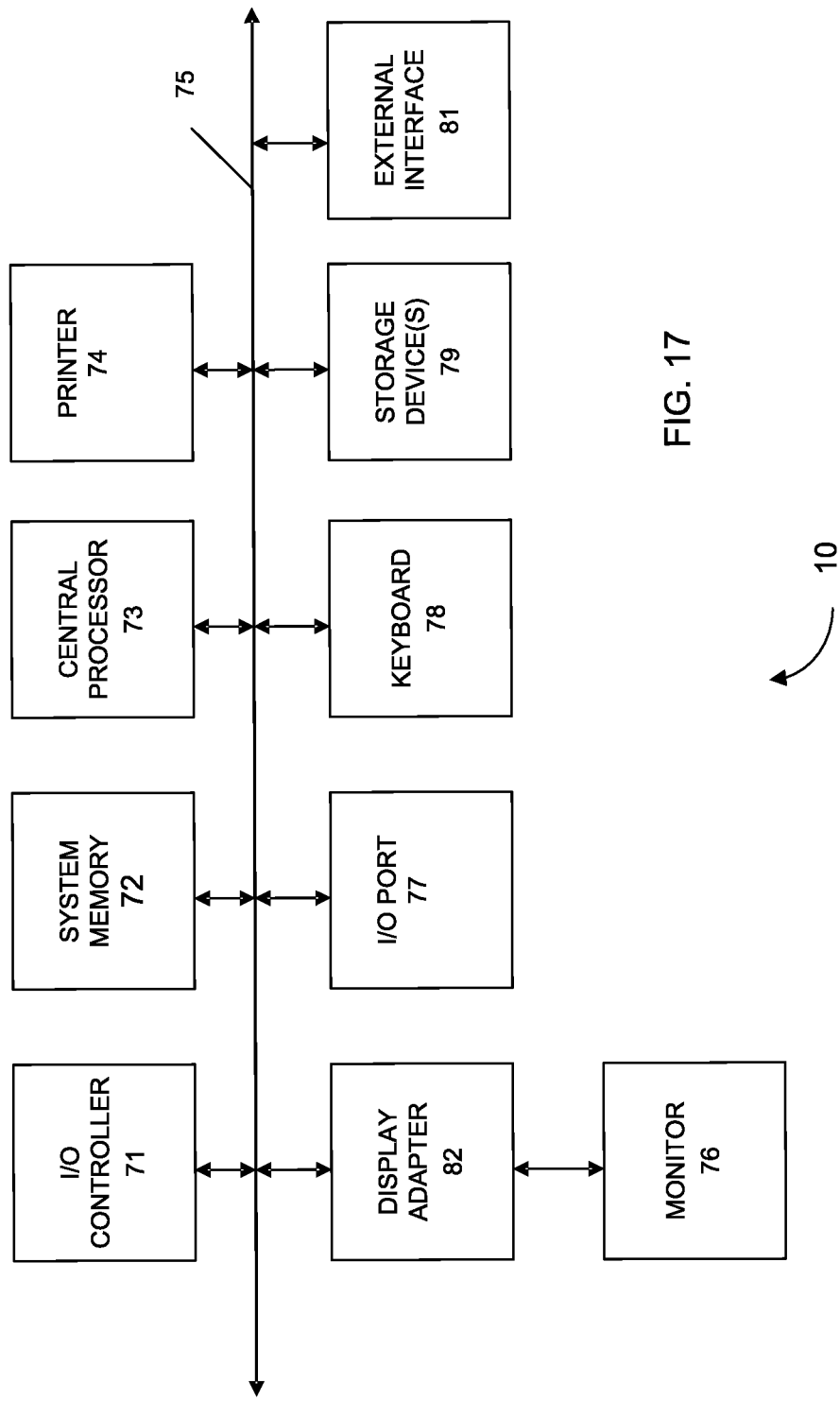
FIG. 17 illustrates an example computer system that can used to implement various embodiments described and illustrated herein.

Any of the computer systems mentioned herein may utilize any suitable number of subsystems. Examples of such subsystems are shown in FIG. 17 in computer system 10, which can be configured to implement various features and/or functions described herein. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 17 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

Two states are also for illustration purpose. It is possible for an embodiment where remote command and local command for changing oxygen device settings be accepted without state switches.

All patents, patent applications, publications, and descriptions mentioned herein are incorporated by reference in their entirety for all purposes. None is admitted to be prior art.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. An oxygen supply device comprising an air separation unit,
   a gas conditioning unit, and a gas delivery unit, wherein
   the air separation unit is configured to receive ambient air, and output concentrated oxygen;
   the gas conditioning unit is configured to receive the concentrated oxygen, receive ambient air, and output blended gas;
   the gas delivery unit is configured to receive blended gas and facilitate a delivery of the blended gas to a user; and, wherein the air separation unit, and the gas conditioning unit are located within a same housing of the oxygen supply device;
   a compression unit configured to compress ambient air for injection into the air separation unit; and, wherein the compression unit is controllable such that a workload of the compression unit is adjustable base on a preset threshold, wherein the compression unit is configured to compress ambient air for injection into the gas conditioning unit;
   a heat exchanger arranged between the compression unit and the air separation unit, wherein the heat exchanger is configured to facilitate heat exchange between a medium around the compression unit and a medium around the air separation unit; and
   a heat communication arranged between the heat exchanger and the gas conditioning unit, where the heat communication is configured to transmit heat to the gas conditioning unit for conditioning gas delivered to the patient.

2. The oxygen supply device of claim 1, wherein the air separation unit comprises one or more oxygen concentration subunits including a first oxygen concentration subunit, the first oxygen concentration subunit comprises a material configured to adsorb oxygen in the ambient air.

3. The oxygen supply device of claim 1, wherein air separation unit is configured to release the enriched oxygen in a pulsing mode.

4. The oxygen supply device of claim 1, wherein the air separation unit comprises one or more oxygen concentration subunits including a first oxygen concentration subunit, the first oxygen concentration subunit comprises a material configured to adsorb nitrogen in the ambient air.

5. The oxygen supply device of claim 1, wherein the gas conditioning unit is configured to be controllable such that ambient air reception is selectable to the gas conditioning unit.

6. A method for controlling an oxygen supply device comprising an air separation unit, a gas conditioning unit, and a gas delivery unit, wherein the method is being implemented by a processor in the oxygen supply device and comprises:
   controlling the air separation unit to receive ambient air, and output concentrated oxygen;
   controlling the gas conditioning unit to receive the concentrated oxygen, receive ambient air, and output blended gas;
   controlling the gas delivery unit to receive blended gas and facilitate a delivery of the blended gas to a user; and, wherein the air separation unit and the gas conditioning unit are located within a same housing of the oxygen supply device;
   compressing ambient air for injection into the air separation unit;
   adjusting a workload of the compression unit base on a preset threshold;
   facilitating heat exchange between a medium around the compression unit and a medium around the air separation unit; and
   transmitting heat to the gas conditioning unit for conditioning gas delivered to the patient.

7. The method of claim 6, wherein the air separation unit comprises one or more oxygen concentration subunits including a first oxygen concentration subunit, the first oxygen concentration subunit comprises a material configured to adsorb oxygen in the ambient air; and wherein the method further comprises controlling the first oxygen concentration subunit to start or stop absorbing the oxygen in the ambient air.

8. The method of claim 6, wherein the method further comprises controlling the air separation unit to release the oxygen enriched gas in a pulsing mode.

9. The method of claim 6, wherein the air separation unit comprises one or more oxygen concentration subunits including a first oxygen concentration subunit, the first oxygen concentration subunit comprises a material configured to adsorb nitrogen in the ambient air; and, wherein the method further comprises controlling the first oxygen concentration subunit to start or stop absorbing the nitrogen in the ambient air.

10. The method of claim 6, further comprising controlling the gas conditioning unit to stop or start receiving ambient air.

* * * * *